(12) United States Patent
Friesen et al.

(10) Patent No.: US 7,375,112 B2
(45) Date of Patent: May 20, 2008

(54) COMPOUNDS AND METHODS FOR REGULATING TRIGLYCERIDE LEVELS

(75) Inventors: Albert D. Friesen, Winnipeg (CA); Marjorie Zettler, Winnipeg (CA)

(73) Assignee: Medicure International Inc., St. James (BB)

( * ) Notice: Subject to any disclaimer, the term of this patent is extended or adjusted under 35 U.S.C. 154(b) by 0 days.

(21) Appl. No.: 11/326,201

(22) Filed: Jan. 5, 2006

(65) Prior Publication Data

US 2006/0148763 A1    Jul. 6, 2006

Related U.S. Application Data

(60) Provisional application No. 60/664,950, filed on Mar. 25, 2005, provisional application No. 60/641,138, filed on Jan. 5, 2005.

(51) Int. Cl.
- A01N 43/42 (2006.01)
- A01N 43/40 (2006.01)
- A61K 31/44 (2006.01)

(52) U.S. Cl. ............................ 514/302; 514/345
(58) Field of Classification Search ............... 514/345, 514/302
See application file for complete search history.

(56) References Cited

U.S. PATENT DOCUMENTS

| | | | |
|---|---|---|---|
| 2,918,471 A * | 12/1959 | Mowat et al. .............. 546/116 |
| 3,282,778 A | 11/1966 | Lobel |
| 3,573,286 A * | 3/1971 | Zenno et al. .............. 546/300 |
| 5,130,252 A * | 7/1992 | Eck et al. .................. 435/280 |
| 6,043,259 A | 3/2000 | Dhalla et al. |
| 6,051,587 A | 4/2000 | Dakashinamurti et al. |
| 6,339,085 B1 * | 1/2002 | Haque .................... 514/233.8 |
| 6,417,204 B1 | 7/2002 | Haque |
| 6,489,345 B1 * | 12/2002 | Sethi et al. ................ 514/332 |
| 6,548,519 B1 | 4/2003 | Haque |
| 6,585,414 B2 | 7/2003 | Peska |
| 6,586,414 B2 | 7/2003 | Haque et al. |
| 6,605,612 B2 | 8/2003 | Haque |
| 6,667,315 B2 | 12/2003 | Haque |
| 6,677,356 B1 * | 1/2004 | Sethi et al. ................ 514/321 |
| 6,780,997 B2 | 8/2004 | Haque |
| 6,861,439 B2 | 3/2005 | Haque et al. |
| 6,867,215 B2 | 3/2005 | Haque |
| 6,890,943 B2 | 5/2005 | Haque |
| 6,897,228 B2 | 5/2005 | Haque |
| 7,105,673 B2 | 9/2006 | Haque |
| 7,115,625 B2 | 10/2006 | Sethi et al. |
| 7,115,626 B2 | 10/2006 | Sethi et al. |
| 7,125,889 B2 | 10/2006 | Sethi et al. |
| 7,132,430 B2 | 11/2006 | Sethi et al. |
| 7,144,892 B2 | 12/2006 | Sethi et al. |
| 7,148,233 B2 | 12/2006 | Sethi et al. |
| 7,230,009 B2 | 6/2007 | Haque et al. |
| 2001/0056081 A1 * | 12/2001 | Haque et al. .............. 514/81 |
| 2003/0114424 A1 | 6/2003 | Haque et al. |
| 2004/0038945 A1 * | 2/2004 | Sethi et al. ................ 514/89 |
| 2004/0121988 A1 | 6/2004 | Haque et al. |
| 2004/0171588 A1 | 9/2004 | Haque |
| 2004/0186077 A1 | 9/2004 | Diakur et al. |
| 2004/0235907 A1 | 11/2004 | Sethi |
| 2005/0107443 A1 | 5/2005 | Haque |
| 2006/0019929 A1 | 1/2006 | Friesen |
| 2006/0035864 A1 | 2/2006 | Friesen |
| 2006/0094748 A1 | 5/2006 | Haque et al. |
| 2006/0094749 A1 | 5/2006 | Haque et al. |
| 2006/0094761 A1 | 5/2006 | Haque et al. |
| 2006/0241083 A1 | 10/2006 | Diakur et al. |
| 2007/0032456 A1 | 2/2007 | Friesen |
| 2007/0060549 A1 | 3/2007 | Friesen |
| 2007/0142270 A1 | 6/2007 | Haque et al. |
| 2007/0149485 A1 | 6/2007 | Friesen |
| 2007/0167411 A1 | 7/2007 | Reimer |
| 2007/0243249 A1 | 10/2007 | Reimer |
| 2007/0249562 A1 | 10/2007 | Reimer |

FOREIGN PATENT DOCUMENTS

| | | | |
|---|---|---|---|
| DE | 2717478 | * | 11/1978 |
| DE | 4344751 | * | 6/1995 |
| JP | 45011700 | * | 4/1970 |
| JP | 45015984 | * | 6/1970 |
| JP | 45016218 | * | 6/1970 |

(Continued)

OTHER PUBLICATIONS

Aguilar-Salinas et l., "Prevalence and characteristics of early-onset type 2 diabetes in mexico", American Journal of Medicine, 2002, vol. 113, pp. 569-574.*

(Continued)

Primary Examiner—Margaret D. Seaman
Assistant Examiner—Niloofar Rahmani
(74) Attorney, Agent, or Firm—Merchant & Gould P.C.

(57) ABSTRACT

The present invention provides a method of administering vitamin B6 related compounds for treatment of hypertriglyceridemia. Vitamin B6 related compounds include pyridoxal, pyridoxal-5'-phosphate, pyridoxamine, a 3-acylated analogue of pyridoxal, a 3-acylated analogue of pyridoxal-4,5-aminal, and mixtures thereof. Embodiments of the present invention also comprise co-administering a lipid lowering agent, such as a nicotinic acid, a fibrate, a HMG CoA reductase inhibitor, a cholesteryl ester transfer protein inhibitor, and combinations thereof.

19 Claims, 4 Drawing Sheets

FOREIGN PATENT DOCUMENTS

| | | | |
|---|---|---|---|
| JP | 45016711 | * | 6/1970 |
| JP | 45016712 | * | 6/1970 |
| JP | 47003830 | * | 2/1972 |
| WO | 2004/084895 | * | 7/2004 |
| WO | 2004/084910 | * | 7/2004 |
| WO | WO 2005/060975 | | 7/2005 |
| WO | WO 2006/005173 | | 1/2006 |
| WO | WO 2006/026868 | | 3/2006 |
| WO | WO 2006/056079 | | 6/2006 |
| WO | WO 2006/058411 | | 6/2006 |
| WO | WO 2006/102748 | | 10/2006 |

OTHER PUBLICATIONS

Harada et al., "Vitamin B6. V. Behavior of orally administered pyridoxal acylates in the blood", Bitamin, 1972, vol. 45, pp. 76-80.*
Harada et al., "Vitamin B6. IV. behavior of pyridoxal acylates in the body after parenteral administration", Bitamin, 1972, vol. 45, pp. 69-75, abstract only see CA 1972: 428787 (AN 77:28747).*
Heyl et al., "phosphates of the vitamin B6 group. II. 3-pyridoxalphosphoric acid", Journal of the american chemistry society, 1951, vol. 73, pp. 3434-3436.*
Heyl et al., "phosphates of the vitamin B6 group. I. The structure of codecarboxylase", Journal of the american chemical society, 1951, vol. 73, pp. 3430-3433.*
Assmann et al., "Relation of High-Density Lipoprotein Cholesterol and Triglycerides to Incidence of Atherosclerotic Coronary Artery Disease (The PROCAM Experience)" Journal of American Cardiology 70 (1992) p. 733-737.
Assmann et al., "Genetic (Primary) Forms of Hypertriglyceridemia" The American Journal of Cardiology. vol. 68 (1991) p. 13a-16a.
Attman et al., "Lipid Abnormalities in Progressive Renal Insufficiency" Contrib. Nephrol. vol. 120 (1997) p. 1-10.
Austin et al., "Hypertriglyceridemia as a Cardiovascular Risk Factor" American Journal of Cardiology 81(4A) (1998) p. 7B-12B.
Berge et al., "Pharmaceutical Salts" Journal of Pharmaceutical Sciences vol. 66, No. 1 (1997) p. 1-19.
Coughlan et al., "Does hyperglyceridemia increase risk for CAD? Growing evidence suggests it plays a role" Postgraduate Medicine vol. 108 No. 7 (2000) p. 77-84.
Di Martino et al., "Severe acute pancreatitis related to the use fo nelfinavir in HIV infection: report of a case with positive rechallange" AIDS vol. 13 No. 11 (1999) p. 1421-1423.
Elisaf et al., "Tamoxifen-induced severe hypertriglyceridemia and pancreatitis" Annals of Oncology 11: (2000) p. 1067-1069.
Fogari et al., "Plasma Lipids During Chronic Antihypertensive Therapy with Different β-Blockers" Journal of Cardiovascular Pharmacology 14 (Suppl. 7) (1989) p. 328-332.
Gaulin et al., "Clozapine-Associated Elevation in Serum Triglycerides" American Journal of Psychiatry 156:8 (Aug. 1999) p. 1270-1272.
Gaspard et al., "A randomized study on the influence of oral contraceptives containing ethinylestradiol combined with drospirenone or desogestrel on lipid and lipoprotein metabolism over a period of 13 cycles" Contraception 69 (2004) p. 271-278.
Greene et al., "Hyperlipidemia and fatty acid composition in patients treated for type IA glycogen storage disease" Journal of Pediatrics, vol. 119 No. 3 (1991) p. 398-403.
Groth et al., "Sirolimus (Rapamycin)-Based Therapy in Human Renal Transplantation, Similar Efficacy and Different Toxicity Compared with Cyclosporine" Transplantation, vol. 67 No. 7 (Apr. 1999) p. 1036-1042.
Jeppesen et al., "Triglyceride Concentration and Ischemic Heart Disease, An Eight Year Follow-up in the Copenhagen Male Study" Circulation 97 (1998) p. 1029-1036.
Kreisberg., "Diabetic Dyslipidemia" The American Journal of Cardiology vol. 82 (12A) (1998) p. 67U-73U.
Kvetny et al., "Subclinical hypothyroidism is associated with a low-grade inflammation, increased trygliceride levels and predicts cardiovascular disease in males below 50 years" Clinical Endocrinology 61 (2004) p. 232-238.

Lindholm et al., "Metabolic outcome during 1 year in newly detected hypertensives: results of the Antihypertensive Treatment and Lipid Profile in a North of Sweden Efficacy Evaluation (ALPINE Study)" Journal of Hypertension vol. 21 No. 8 (2003) p. 1563-1574.
Mancini et al., "Acquired (Secondary) Forms of Hypertriglyceridemia" The American Journal of Cardiology vol. 68, (Jul. 1991) p. 17A-21A.
Mantel-Teeuwisse et al. "Drug-Induced Lipid Changes, A review of the Unintended Effects of Some Commonly Used Drugs on Serum Lipid Levels" Drug Safety 24 (6) (2001) p. 443-456.
Matteucci et al., "An Early Diagnosis of Kidney Involvement in Immunologically-mediated Multisystem Diseases" Clinical Rheumatology 15, No. I (1996) p. 20-24.
Miller et al., "Quantitative and Qualitative Changes in Lipids, Lipoproteins, Apolipoprotein A-I, and Sex Hormone-Binding Globulin Due to Two Doses of Conjugated Equine Estrogen With and Without a Progestin" Obstetrics & Gynecology vol. 83, No. 2 (Feb. 1994) p. 173-179.
Mirete et al., "Acute Pancreatitis as a Complication of Ritonavir Therapy in a Patient with AIDS" European Journal of Clinical Microbiol Infectious Diseases vol. 17 (1998) p. 810-811.
Oda et al., "Lipid abnormalities in end stage renal disease" Nephrology Dialysis Transplantation 13 [Suppl 1] (1998) p. 45-49.
Paisey et al., "Hypertriglyceridaemia in AlströSyndrome: causes and associations in 37 cases" Clinical Endocrinology 60 (2004) p. 228-231.
Pirwany et al., "Lipids and lipoprotein subfractions in women with PCOS: relationship to metabolic and endocrine parameters" Clinical Endocrinology 54 (2001) p. 447-453.
Rader et al., "Management of Selected Lipid Abnormalities, Hypertriglyceridemia, Low HDL Cholesterol, Lipoprotein(a), in Thyroid and Renal Diseases, and Post-Transplantation" Medical Clinics of North America vol. 84 No. 1 (Jan. 2000) p. 43-61.
Ravid et al., "Plasma lipids and the progression of nephropathy in diabetes mellitus type II: Effects of ACE inhibitors" Kidney International vol. 47 (1995) p. 907-910.
Roberts et al., "Alterations in Serum Levels of Lipids and Lipoproteins with Indinavir Therapy for Human Immunodeficiency Virus-Infected Patients" Clinical Infectious Diseses 29 (1999) p. 441-443.
Schmidt et al., "Clustering of Dyslipidemia, Hyperuricemia, Diabetes, and Hypertension and Its Association with Fasting Insulin and Central and Overall Obesity in a General Population" Metabolism vol. 45, No. 6. (Jun. 1996) p. 699-706.
Scharnagl et al., "Double-blind, randomized study comparing the effects of two monophasic oral contraceptives containing ethinylestradiol (20 μg or 30 μg) and levonorgestrel (100 μg or 150 μg) on lipoprotein metabolism" Contraception 69 (2004) p. 105-113.
van der Heijden et al., "A Randomized, Placebo-Controlled Study of Loop Diuretics in Patients with Essential Hypertension: The Bumetanide and Furosemide on Lipid Profile (BUFUL) Clinical Study Report" Journal of Clinical Pharmacology 38 (1998) p. 630-635.
Vahlquist et al., "Serum Lipid Changes during Acitretin (Etretin) Treatment of Psoriasis and Palmo-plantar Pustulosis" Acta Derm Venereol ( Stockh) 68 (1988) p. 300-305.
Zech et al., "Changes in Plasma Cholesterol and Triglyceride Levels After Treatment With Oral Isotretinoin" Arch Dermatol, vol. 119 (Dec. 1983) p. 987-993.
Brousseau et al., "Effects of an Inhibitor of Cholesterol Ester Transfer Protein on HDL Cholesterol," *N. Engl. J. Med.* 2004, 350: 1505-1515.
de Grooth et al., "Efficacy and Safety of a Novel Cholesteryl Ester Transfer Protein Inhibitor, JTT-705 in Humans," *Circulation* 2002, 105:2159-2165.
Lipsy, "Overview of Pharmacological Therapy for the Treatment of Dyslipidemia," *J Manag Care Pharm.* 2003, 9 (1 Suppl): 9-12. (Abstract Only).

Cruz et al., "The Metabolic Syndrome in Overweight Hispanic Youth and the Role of Insulin Sensitivity", *The Journal of Clinical Endocrinology & Metabolism*, 89(1):108-113 (2004).

Glenberg, "Measuring the Strength of Linear Relationships: Correlation", Learning From Data: An Introduction to Statistical Reasoning, Second Edition, Lawrence Erlbaum Associates, Publishers, Ch. 21, pp. 475-501 (1996).

Kuivenhoven et al., "Effectivness of Inhibition of Cholesteryl Ester Transfer Portein by JTT-705 in Combination with *Pravastatin* in Type II Dyslipidemia", *The American Journal of Cardiology*, 95:1085-1088 (2005).

Van der Steeg et al., "Role of CETP Inhibitors in the treatment of dyslipidemia", *Current Opinion in Lipidology*, 15:631-636 (2004).

* cited by examiner

COMPOUNDS AND METHODS FOR REGULATING TRIGLYCERIDE LEVELS

CROSS-REFERENCE TO RELATED APPLICATION

This application claims the benefit under 35 U.S.C. § 119(e) of U.S. Provisional Patent Application Ser. No. 60/641,138, filed Jan. 5, 2005, and of U.S. Provisional Patent Application Ser. No. 60/664,950, filed Mar. 25, 2005, the entire disclosures of which are hereby incorporated by referece.

FIELD OF INVENTION

The present invention relates to compounds and methods for regulating triglyceride levels.

BACKGROUND

One of the major causes of atherosclerosis and the related diseases, coronary heart disease (CHD), peripheral arterial disease (PAD), and cerebrovascular disease, is dyslipidemia. Dyslipidemia is an imbalance of each of the lipid components: total cholesterol (TC), high density lipoprotein (HDL) cholesterol, low density lipoprotein (LDL) cholesterol, and serum triglycerides.

Although it is still debated whether triglycerides have an indirect effect (via increased VLDL, decreased HDL, or enhancement of thrombogenesis) or direct effect on cardiovascular disease, there has been enough evidence accumulated in the last decade to consider high triglyceride serum levels to be independently related and important in measuring the risk of CHD (Austin et al., 1998, *Am. J. Cardiol.*, 81: 7B-12B; Coughlan et al., 2000, *Postgrad. Med.*, 108: 77-84; Rader et al., 2000, *Med. Clin. North Am.*, 84: 43-61).

The PROCAM (The Prospective Cardiovascular Munster 1979-1985) study showed that fasting levels of triglycerides were an independent risk factor for CHD when excessive triglycerides are paired with high LDL and low HDL levels (Assmann et al., 1992, *Am. J. Cardiol.*, 70: 733-737). The chance of a major coronary event was statistically significantly decreased with lowered triglyceride levels (Assmann et al., 1992). The Copenhagen Male Study also confirmed the results of the PROCAM study (Jeppesen et al., 1998, *Circulation*, 97: 1029-1036). The 3000 participant study showed that men who had triglyceride levels in the upper third region were 2.2 times more likely to be at risk of developing CHD (Jeppesen et al., 1998).

Normal fasting levels of triglyceride levels are 150 mg/dL and lower (National Cholesterol Education Program (NCEP) Expert Panel on Detection, Evaluation, and Treatment of High Blood Cholesterol in Adults (Adult Treatment Panel III), 2002, *Circulation*, 106:3143-3421). The range of 150 mg/dL to 199 mg/dL is considered borderline high, and levels greater than 200 mg/dL are high (NCEP Expert Panel, 2002). For borderline patients, non-pharmacologic measures are prescribed. This is usually a change in lifestyle including increased exercise, low fat diet and smoking cessation. When levels of triglycerides are greater than 200 mg/dL, drug treatment is given.

Hypertriglyceridemia may be classified as either primary or acquired (Assmann, et al., 1991, *Am. J. Cardiol.*, 68: 13A-16A; Mancini et al., 1991, *Am. J. Cardiol.*, 68: 17A-21A). Primary hypertriglyceridemias are inherited disorders, which include chylomicronemia (type I hyperlipoproteinemia), type V hyperlipoproteinemia, type III hyperlipoproteinemia (remnant hyperlipidemia or familial dysbetalipoproteinemia), familial hypertriglyceridemia, familial combined hyperlipidemia, and hepatic lipase deficiency (Assmann et al., 1991). The severity of the symptoms depends in part on whether the patient is homozygous or heterozygous. Primary hypertriglyceridemias may present as early as childhood. Acquired hypertriglyceridemia may be attributed to many factors, including metabolic disorders such as type II diabetes, metabolic syndome, insulin resistance, pre-diabetes, syndrome X, obesity, hyperuricemia, Alström's syndrome, and type I glycogen storage disease (Kreisberg, 1998, *Am. J. Cardiol.*, 82: 67U-73U; Schmidt et al., 1996, *Metabolism*, 45: 699-706; Paisey et al., 2004, *Clin. Endocrinol.*, 60: 228-231; Greene et al., 1991, *J Pediatr.*, 119: 398-403). These conditions may also present in childhood. Similarly, hormonal disturbances may cause hypertriglyceridemia. In addition to insulin, triglyceride levels may be elevated as a result of hypothyroidism or polycystic ovary syndrome (Kvetny et al., 2004, *Clin. Endocrinol.*, 61: 232-238; Pirwany et al., 2001, *Clin. Endocrinol.*, 54: 447-453).

Acquired hypertriglyceridemia can be due to lifestyle factors such as diet (high sugar or carbohydrate intake) or alcohol consumption (Coughlan et al., 2000). Chronic disease states such as renal disease (including nephrotic syndrome and renal failure) or paraproteinemia can also cause elevated triglycerides (Attman et al., 1997, *Contrib. Nephrol.*, 120:1-10; Oda et al., 1998, *Nephrol. Dial. Transplant.*, 13:45-49; Matteucci et al., 1996, *Clin. Rheumatol.*, 15:20-24.). These disorders may also manifest in childhood. Finally, a number of different drugs can raise triglyceride levels (*Drug Ther Perspect*, 2001, 17:11-15; Mantel-Teeuwisse et al., 2001, *Drug Saf.*, 24:443-456), including diuretics (including thiazide (Lindholm et al., 2003, *J. Hypertens.*, 21:1563-1574) and loop diuretics (van der Heijden et al., 1998, *J. Clin. Pharmacol.*, 38:630-635); β-blockers (Fogari et al., 1989, *J. Cardiovasc. Pharmacol.*, 14:S28-S32); angiotensin converting enzyme inhibitors (Ravid et al., 1995, *Kidney Int.*, 47:907-910); estrogen replacement therapy (Miller et al., 1994, *Obstet. Gynecol.*, 83:173-179.); oral contraceptives with second and third generation progestogens (Scharnagl et al., 2004, *Contraception*, 69:105-113; Gaspard et al., 2004, *Contraception.*, 69:271-278); estrogen receptor modulators (such as tamoxifen (Elisaf et al., 2000, *Ann. Oncol.*, 11: 1067-1069)); retinoids (such as isotretinoin (Zech et al., 1983, *Arch. Dermatol.*, 119:987-993) and acitretin (Vahlquist et al., 1988, *Acta Derm. Venereol.*, 68:300-305)); immunosuppressive drugs (such as rapamycin (Groth et al., 1999, *Transplantation*, 67:1036-1042)); protease inhibitors (such as ritonavir (Mirete et al., 1998, *Eur. J. Clin. Microbiol. Infect. Dis.*, 17:810-811), indinavir (Roberts et al., 1999, *Clin. Infect. Dis.*, 29:441-443) and nelfinavir (Di Martino et al., 1999, *AIDS*, 13:1421-1423)); and antipsychotics (such as clozapine (Gaulin et al., 1999, *Am. J. Psychiatry*, 156: 1270-1272)).

The three main treatment options for hypertriglyceridemia are statins, fibrates, and niacin. While statins are the most commonly prescribed drug for hyperlipidemia, they are not usually given unless the patient also has high LDL levels. Statins only give a marginal (10-30%) reduction in triglycerides. This decrease is dependent on the type of statin given. Nicotinic acid gives better reductions in triglycerides than statins. On average, a 20% to 40% reduction of triglycerides can be seen with low doses of niacin. Side effects from niacin include mild to moderate flushing and hyperglycemia and hepatic toxicity with higher doses. These side effects prevent niacin from being suitable for a large population, especially diabetics. Fibrates are the most effective triglyceride lowering agents. The average reduction with fibrate treatment is 20% to 55%. The major side effect of fibrates is gastrointestinal discomfort, which occurs in up to 10% of patients.

Current lipid lowering therapies do not sufficiently address the high triglyceride levels that are now known to be an important risk factor for cardiovascular disease without unwanted side effects.

SUMMARY OF INVENTION

In a first aspect, the invention provides a method of treating and preventing hypertriglyceridemia comprising administering a therapeutically effective amount of a vitamin B6 related compound or a pharmaceutically acceptable salt thereof to a patient in need thereof.

In a second aspect, the invention provides a use of a therapeutically effective amount of a vitamin B6 related compound or a pharmaceutically acceptable salt thereof for the treatment and prevention of hypertriglyceridemia in a patient in need thereof.

In a third aspect, the invention provides a kit comprising: (a) a pharmaceutical preparation for administration comprising a compound selected from the group consisting of pyridoxal, pyridoxal-5'-phosphate, pyridoxamine, a 3-acylated analogue of pyridoxal, and a 3-acylated analogue of pyridoxal-4,5-aminal; and (b) instructions for the administration of said preparation, said instructions specifying that said preparation should be administered for the treatment or prevention of hypertriglyceridemia.

In an embodiment of the invention, the instructions further specify that the preparation should be administered in combination with a lipid lowering agent selected from the group consisting of a nicotinic acid, a fibrate, a HMG CoA reductase inhibitor, a cholesteryl ester transfer protein inhibitor, and a combination thereof.

In an embodiment of the invention, the instructions further specify that the preparation should be administered in combination with an ACE inhibitor selected from the group consisting of benazepril; captopril; cilazapril; enalapril; enalaprilat; fosinopril; lisinopril; moexipril; perindopril; quinapril; ramipril; trandolapril; and a mixture thereof.

In an embodiment of the invention, a vitamin B6 related compound is selected from the group consisting of pyridoxal, pyridoxal-5'-phosphate, pyridoxamine, a 3-acylated analogue of pyridoxal, a 3-acylated analogue of pyridoxal-4,5-aminal, and a mixture thereof.

In another embodiment of the invention, the vitamin B6 related compound is pyridoxal-5-phosphate.

In a further embodiment of the invention, the 3-acylated analogue of pyridoxal is:

wherein
  $R_1$ is alkyl,
  alkenyl,
    in which alkyl or alkenyl
      can be interrupted by nitrogen, oxygen, or sulfur, and
      can be unsubstituted or substituted at the terminal carbon
      by hydroxy, alkoxy, alkanoyloxy, alkanoyloxyaryl, alkoxyalkanoyl, alkoxycarbonyl, or dialkylcarbamoyloxy;
  alkoxy;
  dialkylamino;
  alkanoyloxy;
  alkanoyloxyaryl;
  alkoxyalkanoyl;
  alkoxycarbonyl;
  dialkylcarbamoyloxy;
  aryl,
    in which aryl can be substituted by alkyl, alkoxy, amino, hydroxy, halo, nitro, or alkanoyloxy;
  aryloxy;
  arylthio; or
  aralkyl, or a pharmaceutically acceptable acid addition salt thereof.

In a further embodiment of the invention, the 3-acylated analogue of pyridoxal-4,5-aminal is wherein
  $R_1$ is alkyl,
  alkenyl,
    in which alkyl or alkenyl
      can be interrupted by nitrogen, oxygen, or sulfur, and
      can be unsubstituted or substituted at the terminal carbon
      by hydroxy, alkoxy, alkanoyloxy, alkanoyloxyaryl, alkoxyalkanoyl, alkoxycarbonyl, or dialkylcarbamoyloxy;
  alkoxy;
  dialkylamino;
  alkanoyloxy;
  alkanoyloxyaryl;
  alkoxyalkanoyl;
  alkoxycarbonyl;
  dialkylcarbamoyloxy;
  aryl,
    in which aryl can be substituted by alkyl, alkoxy, amino, hydroxy, halo, nitro, or alkanoyloxy;
  aryloxy;
  arylthio; or
  aralkyl; and $R_2$ is of the formula wherein $R_3$ and $R_4$ are each independently alkyl, alkenyl, cycloalkyl, aryl, or, when $R_3$ and $R_4$ are taken together to form a ring with the nitrogen atom, which may optionally be interrupted by a heteroatom, or a pharmaceutically acceptable acid addition salt thereof.

In an embodiment of the invention, hypertriglyceridemia is primary hypertriglyceridemia.

In a further embodiment of the invention, the patient has a metabolic disorder such as diabetes, insulin resistance, pre-diabetes, syndrome X, obesity, hyperuricemia, Alström's syndrome, and type I glycogen storage disease.

In a further embodiment of the invention, the patient has a hormonal disturbance such as hypothyroidism, polycystic ovary disorder, Cushing's syndrome, acromegaly and pregnancy.

In a further embodiment of the invention, the patient has a renal disease such as renal insufficiency or nephrotic syndrome.

In a further embodiment of the invention, the patient has an immunological disorder such as paraproteinemia, dysgammaglobulinemia, and systemic lupus erythematosus.

In an embodiment of the invention, hypertrigylceridemia is secondary hypertriglyceridemia.

In a further embodiment of the invention, the secondary hypertriglyceridemia is drug related. A drug may be: alcohol, a diuretic, a β-blocker, an angiotensin converting enzyme inhibitor, an estrogen replacement therapy, an oral contraceptive, an estrogen receptor modulator, a retinoid, an immunosuppressant, an antiretroviral, a protease inhibitor, an antipsychotic, and combinations thereof.

In an embodiment of the invention, the therapeutically effective amount of pyridoxal-5'-phosphate is between 0.5 and 50 mg/kg body weight.

In an embodiment of the invention, the therapeutically effective amount of pyridoxal-5'-phosphate is between 1 and 15 mg/kg body weight.

In an embodiment of the invention, the patient is human.

In an embodiment of the invention, the method of treating and preventing hypertriglyceridemia, further comprises administering a therapeutically effective amount of a lipid lowering agent selected from the group consisting of a nicotinic acid, a fibrate, a HMG CoA reductase inhibitor, a cholesteryl ester transfer protein inhibitor, and a combination thereof, to the patient in need thereof.

In an embodiment of the invention, the method of treating and preventing hypertriglyceridemia further comprises a lipid lowering agent selected from the group consisting of a nicotinic acid, a fibrate, a HMG CoA reductase inhibitor, and a combination thereof In a further embodiment of the invention, the nicotinic acid is niacin.

In a further embodiment of the invention, the fibrate is selected from the group consisting of bezafibrate, clofibrate, ciprofibrate, fenofibrate, and gemifibrozil, and a mixture thereof.

In a further embodiment of the invention, the HMG CoA reductase inhibitor is selected from the group consisting of pravastatin, lovastatin, fluvastatin, atorvastatin, simvastatin, rosuvastatin, velostatin, fluindostatin, and a mixture thereof.

In a further embodiment of the invention, the cholesteryl ester transfer protein inhibitor is torcetrapib (Pfizer) or JTT-705 (Japan Tobacco).

In an embodiment of the invention, the method of treating and preventing hypertriglyceridemia, further comprises administering a therapeutically effective amount of an ACE inhibitor selected from the group consisting of benazepril; captopril; cilazapril; enalapril; enalaprilat; fosinopril; lisinopril; moexipril; perindopril; quinapril; ramipril; trandolapril; and a mixture thereof.

In a further embodiment of the invention, the ACE inhibitor is lisinopril.

In a further embodiment of the invention, the therapeutically effective amount of lisinopril is between 5 and 40 mg per day.

In a further embodiment of the invention, the therapeutically effective amount of lisinopril is 20 mg per day.

DETAILED DESCRIPTION

Vitamin B6 related compounds such as P5P are effective for selectively lowering serum levels of triglycerides. Embodiments of the instant invention provide the use of a vitamin B6 related compound or a pharmaceutically acceptable salt thereof for treating individuals at risk for developing hypertriglyceridemia and individuals having hypertriglyceridemia. The methods of treatment according to the present invention encompass the use of vitamin B6 related compounds alone or in combination with an additional lipid lowering agent for the reduction of serum levels of triglycerides.

Where the patient to be treated is human, the term "hypertriglyceridemia" refers to fasting serum levels of triglycerides of >150 mg/dL. The term "hypertriglyceridemia" encompasses both primary and secondary forms of hypertriglyceridemia.

Examples of types of primary hypertriglyceridemia which may be treated using a vitamin B6 related compound or a pharmaceutically acceptable salt thereof include, but are not limited to: familial lipoprotein lipase (LPL) deficiency (Type I); familial apo C-II deficiency (Type I); familial dysbetalipoproteinemia (Type III); familial hypertriglyceridemias (Type IV and Type V); and familial combined hyperlipidemia (Types IIa, IIb & IV).

The invention also encompasses the use of a vitamin B6 related compound or a pharmaceutically acceptable salt thereof for treating secondary or acquired hypertriglyceridemia in patients suffering: (1) a metabolic disorder such as obesity, type II diabetes, insulin resistance, pre-diabetes, syndrome X, metabolic syndrome; Alström's syndrome, hyperuricemia and type I glycogen storage disease; (2) a renal disorder such as renal insufficiency, nephrotic syndrome; (3) a hormonal disturbance such as hypothyroidism, Cushing's syndrome, acromegaly, polycystic ovary disorder and pregnancy, and (4) an immunological disorder such as paraproteinemia, dysgammaglobulinemias, and systemic lupus erythematosus.

Vitamin B6 related compounds are also useful for treating secondary or acquired hypertriglyceridemia resulting from drug use. Examples of drugs associated with secondary hypertriglyceridemia include but are not limited to: alcohol, diuretics (including thiazide, loop and potassium sparing diuretics), β-blockers, angiotensin converting enzyme (ACE) inhibitors, estrogen replacement therapy, oral contraceptives, estrogen receptor modulators (such as tamoxifen and raloxifene), glucocorticoid steroids, retinoids (such as isotretinoin and acitretin), immunosuppressants, antiretrovirals, protease inhibitors (such as ritonavir, indinavir, and nelfinavir), and antipsychotics (such as clozapine).

As used herein, "vitamin B6 related compound", means any vitamin B6 precursor, metabolite, derivative, or analogue thereof but explicitly excludes: (1) vitamin B6 (pyroxidine) and (2) magnesium pyridoxal 5'-phosphate glutamate. Examples of vitamin B6 related compounds which may be used to practice the method according to the invention include but are not limited to pyridoxal-5-phosphate (P5P), pyridoxal, and pyridoxamine. Other vitamin B6 related compounds, which can also be used, include the 3-acylated analogues of pyridoxal, 3-acylated analogues of pyridoxal-4,5-aminal, and pyridoxine phosphonate analogues as disclosed in U.S. Pat. No. 6,585,414 and U.S. patent application Ser. No. 20030114424, both of which are incorporated herein by reference. Preferably, the vitamin B6 related compound will be P5P.

The 3-acylated analogue of pyridoxal includes:

wherein
R₁ is alkyl,
alkenyl,
in which alkyl or alkenyl
can be interrupted by nitrogen, oxygen, or sulfur, and
can be unsubstituted or substituted at the terminal carbon
by hydroxy, alkoxy, alkanoyloxy, alkanoyloxyaryl, alkoxyalkanoyl, alkoxycarbonyl, or dialkylcarbamoyloxy;
alkoxy;
dialkylamino;
alkanoyloxy;
alkanoyloxyaryl;
alkoxyalkanoyl;
alkoxycarbonyl;
dialkylcarbamoyloxy;
aryl,
in which aryl can be substituted by alkyl, alkoxy, amino, hydroxy, halo, nitro, or alkanoyloxy;
aryloxy;
arylthio; or
aralkyl, or a pharmaceutically acceptable acid addition salt thereof.

The 3-acylated analogue of pyridoxal-4,5-aminal includes:

wherein
R₁ is alkyl,
alkenyl,
in which alkyl or alkenyl
can be interrupted by nitrogen, oxygen, or sulfur, and
can be unsubstituted or substituted at the terminal carbon
by hydroxy, alkoxy, alkanoyloxy, alkanoyloxyaryl, alkoxyalkanoyl, alkoxycarbonyl, or dialkylcarbamoyloxy;
alkoxy;
dialkylamino;
alkanoyloxy;
alkanoyloxyaryl;
alkoxyalkanoyl;
alkoxycarbonyl;
dialkylcarbamoyloxy;
aryl,
in which aryl can be substituted by alkyl, alkoxy, amino, hydroxy, halo, nitro, or alkanoyloxy;
aryloxy;
arylthio; or
aralkyl; and
R₂ is of the formula wherein R₃ and R₄ are each independently alkyl, alkenyl, cycloalkyl, aryl, or, when R₃ and R₄ are taken together to form a ring with the nitrogen atom, which may optionally be interrupted by a heteroatom, or a pharmaceutically acceptable acid addition salt thereof.

As used herein "alkyl" includes a saturated linear or branched hydrocarbon radical. In one embodiment, alkyl has from 1 to 8 carbon atoms. In another embodiment, alkyl has from 1 to 6 carbon atoms. In another embodiment, alkyl has from 1 to 4 carbon atoms. In one embodiment, alkyl has 1 carbon. The alkyl group may optionally be substituted with one or more substituents such as fluorine, chlorine, alkoxy groups having from 1 to 8 carbon atoms (e.g., methoxy or ethoxy), or amido groups having from 1 to 8 carbon atoms, such as acetamido. These substituents may themselves be substituted with one or more functional groups such as hydroxy groups, carboxy groups, acetoxy groups, or halogens.

The term "alkenyl" group includes an unsaturated aliphatic hydrocarbon chain having from 2 to 8 carbon atoms, such as, for example, ethenyl, 1-propenyl, 2-propenyl, 1-butenyl, 2-methyl-1-propenyl, and the like.

The above alkyl or alkenyl groups may optionally be interrupted in the chain by a heteroatom, such as, for example, a nitrogen, sulfur, or oxygen atom, forming an alkylaminoalkyl or alkoxyalkyl group, for example, methylaminoethyl or methoxymethyl, and the like.

The term "alkoxy" group includes an alkyl group as defined above joined to an oxygen atom having preferably from 1 to 4 carbon atoms in a straight or branched chain, such as, for example, methoxy, ethoxy, propoxy, isopropoxy (1-methylethoxy), butoxy, tert-butoxy (1,1-dimethylethoxy), and the like.

The term "dialkylamino" group includes two alkyl groups as defined above joined to a nitrogen atom, in which the alkyl group has preferably 1 to 4 carbon atoms, such as, for example, dimethylamino, diethylamino, methylethylamino, methylpropylamino, diethylamino, and the like.

As used herein "aryl" means a mono- or poly-nuclear aromatic hydrocarbon radical. Examples of "aryl" groups include, but are not limited to aromatic hydrocarbons such as a phenyl group or a naphthyl group. The aromatic group may optionally be substituted with one or more substituents such as fluorine, chlorine, alkyl groups having from 1 to 8 carbon atoms (e.g., methyl or ethyl), alkoxy groups having from 1 to 8 carbon atoms (e.g., methoxy or ethoxy), alkoxyalkyl groups having from 1 to 8 carbon atoms and one or more oxygen atoms, or amido groups having from 1 to 8 carbon atoms, such as acetamido. These substituents may themselves be substituted with one or more functional groups such as hydroxy groups, carboxy groups, acetoxy groups, or halogens.

In one embodiment, aryl is a phenyl group or a naphthyl group that is either unsubstituted or substituted.

In another embodiment, aryl is a heteroaryl in which one or more of the carbon atoms of an aromatic hydrocarbon is substituted with a nitrogen, sulfur, or oxygen. Examples of a "heteroaryl" include, but are not limited to pyridine, pyrimidine, pyran, dioxin, oxazine, and oxathiazine. Likewise, the heteroaryl may optionally be substituted with functional groups such as hydroxy groups, carboxy groups, halogens, and amino groups.

The term "secondary amino" group includes a group of the formula:

derived from a secondary amine $R_1R_2NH$, in which $R_1$ and $R_2$ are each independently alkyl, alkenyl, cycloalkyl, aryl, or, when $R_1$ and $R_2$ are taken together, may form a ring with the nitrogen atom and which may optionally be interrupted by a heteroatom, such as, for example, a nitrogen, sulfur, or oxygen atom. The terms "alkyl," "alkenyl," and "aryl" are used as defined above in forming secondary amino groups such as, for example, dimethylamino, methylethylamino, diethylamino, dialkylamino, phenylmethylamino, diphenylamino, and the like.

The invention also includes pharmaceutically acceptable salts of the compounds of the invention. The compounds of the invention are capable of forming both pharmaceutically acceptable acid addition and/or base salts. Pharmaceutically acceptable acid addition salts of the compounds of the invention include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and di-carboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glucamine, etc. (see Berge et al., *J. Pharmaceutical Science*, 66: 1-19 (1977)). The term "pharmaceutically acceptable salts" also includes any pharmaceutically acceptable base salt including, but not limited to, amine salts, trialkyl amine salts and the like. Such salts can be formed quite readily by those skilled in the art using standard techniques.

Acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention. Base salts are formed with metals or amines, such as alkali and alkaline earth metals or organic amines. Examples of metals used as cations include, but are not limited to, sodium, potassium, magnesium, and calcium. Examples of suitable amines are N,N'-dibenzylethylenediamine, chloroprocaine, choline, diethanolamine, ethylenediamine, N-methylglucamine, and procaine.

Some of the compounds described herein contain one or more asymmetric centers and this may give raise to enantiomers, disasteriomers, and other stereroisomeric forms which may be defined in terms of absolute stereochemistry as (R)- or (S)-. The present invention is meant to include all such possible diasteriomers and enantiomers as well as their racemic and optically pure forms. Optically active (R)- and (S)-isomers may be prepared using chiral synthons or chiral reagents, or resolved using conventional techniques. When the compounds described herein contain olefinic double bonds or other centres of geometric symmetry, and unless specified otherwise, it is intended that the compounds include both E and A geometric isomers. Likewise all tautomeric forms are intended to be included.

Although it is possible for a compound suitable for use in methods of the invention to be administered alone in a unit dosage form, preferably the compound is administered in admixture as a pharmaceutical composition suitable for use in methods of the invention. A pharmaceutical composition comprises a pharmaceutically acceptable carrier and a compound. A pharmaceutically acceptable carrier includes, but is not limited to, physiological saline, ringers, phosphate buffered saline, and other carriers known in the art. Pharmaceutical compositions may also include additives, for example, stabilizers, antioxidants, colorants, excipients, binders, thickeners, dispersing agents, readsorpotion enhancers, buffers, surfactants, preservatives, emulsifiers, isotonizing agents, and diluents. Pharmaceutically acceptable carriers and additives are chosen such that side effects from the pharmaceutical compound are minimized and the performance of the compound is not canceled or inhibited to such an extent that treatment is ineffective.

Methods of preparing pharmaceutical compositions containing a pharmaceutically acceptable carrier and a compound suitable for use in methods of the invention are known to those of skill in the art. All methods may include the step of bringing the compound in association with the carrier and additives. In general, the formulations are prepared by uniformly and intimately bringing the compound of the invention into association with a liquid carrier or a finely divided solid carrier or both, and then, if necessary, shaping the product into the desired unit dosage form.

It is to be understood that this invention is not limited to specific dosage forms, carriers, or the like, as such may vary. It is also to be understood that the terminology used herein is for the purpose of describing particular embodiments only, and is not intended to be limiting.

In some circumstances it may be desirable to administer the vitamin B6 related compound or its pharmaceutically acceptable salt in combination with a therapeutically effective amount of another lipid lowering agent such as a nicotinic acid (such as niacin), a fibrate (such as bezafibrate, clofibrate, ciprofibrate, fenofibrate, and gemifibrozil), a HMG CoA reductase inhibitor (such as pravastatin, lovastatin, fluvastatin, atorvastatin, simvastatin, rosuvastatin, velostatin, and fluindostatin) or a cholesteryl ester transfer protein (CETP) inhibitor (such as torcetrapib or JTT-705). Combination therapy may be preferable in circumstances, where treatment with a vitamin B6 related compound alone does not lower triglyceride levels to the desired extent.

In some circumstances it may be desirable to administer the vitamin B6 related compound or its pharmaceutically acceptable salt in combination with a therapeutically effective amount of an angiotensin converting enzyme (ACE) inhibitor such as but not limited to: benazepril; captopril; cilazapril; enalapril; enalaprilat; fosinopril; lisinopril; moexipril; perindopril; quinapril; ramipril; trandolapril; or a mixture thereof. In a preferred embodiment, the ACE inhibitor is lisinopril.

In a further preferred embodiment of the invention, the ACE inhibitor component administered is lisinopril and the vitamin B6 related component administered is P5P.

By an "effective" amount or a "therapeutically effective amount" of a drug or pharmacologically active agent is meant a nontoxic but sufficient amount of the drug or agent to provide the desired effect. In the combination therapy of the present invention, an "effective amount" of one component of the combination is the amount of that compound that is effective to provide the desired effect when used in combination with the other components of the combination. The amount that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation.

Vitamin B6 related compounds can be administered orally. Preferred oral dosage forms contain a therapeutically effective unit dose of each active agent, wherein the unit dose is suitable for a once-daily oral administration. The therapeutic effective unit dose of any of the active agents will depend on number of factors, which will be apparent to those skilled in the art and in light of the disclosure herein. In particular these factors include: the identity of the compounds to be administered, the formulation, the route of administration employed, the patient's gender, age, and weight, and the severity of the condition being treated and the presence of concurrent illness affecting the gastrointestinal tract, the hepatobillary system and the renal system. Methods for determining dosage and toxicity are well known in the art with studies generally beginning in animals and then in humans if no significant animal toxicity is observed. The appropriateness of the dosage can be assessed by monitoring triglyceride levels. Where the dose provided does not cause triglyceride levels to decline to normal or tolerable levels, following at least 2 to 4 weeks of treatment, the dose can be increased.

The preferred therapeutically effective amount for the vitamin B6 related compound is between 0.1 to 100 mg/kg body weight daily. Where the vitamin B6 related compound is pyridoxal-5'-phosphate the preferred therapeutically effective amount is between 0.5 and 50 mg/kg body weight and more preferably, between 1 and 15 mg/kg body weight. In circumstances where the vitamin B6 related compound is administered in combination with another lipid lowering agent, the amount of vitamin B6 related compound may be reduced.

In embodiments of the invention, wherein the vitamin B6 related compound is administered with an ACE inhibitor, and more preferably lisinopril, the therapeutically effective amount of the lisinopril is between 5 and 40 mg per day, and more preferably about 20 mg per day.

Although the invention has been described with reference to illustrative embodiments, it is to be understood that the invention is not limited to these precise embodiments, and that various changes and modifications may be effected therein by one skilled in the art. All such changes and modifications are intended to be encompassed by the appended claims.

EXAMPLES

Example 1

P5P Therapy Lowers Blood Pressure and Improves Triglyceride Levels in Hypertensive Diabetics Overview—The study was a 14-week, open-label, forced, dose-escalation study of the efficacy and safety of P5P administered once daily over a dose range of 250 mg to 750 mg, for the treatment of mild to moderate hypertension and hyperlipidemia, in patients with coexisting diabetes mellitus.

Patient Definition—Patients meeting all of the inclusion criteria and none of the exclusion criteria were eligible for enrollment. The primary inclusion criteria were hypertension and diabetes. At screening all patients must have presented with or had a history of, uncomplicated, stable, mild to moderate hypertension, (supine diastolic blood pressure SUDBP $\geq 90$ and $\leq 114$ mm Hg) regardless of use or non-use of treatment for this disease. Additionally, at the end of the 4-week placebo lead-in period, to be eligible for single blind treatment, patients must have demonstrated a mean SUDBP of ≧90 mm Hg and ≦114 mm Hg. The hypertensive patients must have presented with and had a history (>24 months) of diabetes mellitus (type 1 or 2), that was controlled or uncontrolled, at both screening and treatment initiation visits, to be eligible for inclusion in the study. Other than having diabetes and hypertension, patients must have been in good health for their age. A history and physical examination must have been within age-related normal limits, or if abnormal, considered clinically insignificant in the opinion of the investigator. Laboratory tests (CBC with differential, prothrombin and partial thrombo-plastin times, platelet count, and urinalysis and blood chemistry panel), must have been normal, or if abnormal, considered clinically insignificant. Patients must have had a normal ECG or, if abnormal, considered clinically insignificant.

Exclusion criteria included the presence or history (past 12 months) of accelerated or malignant hypertension, as evidenced by hemorrhage and/or exudate, and/or papilloedema on funduscopic examination. Patients having a history of angioedema of the face, lips, tongue, glottis or larynx when treated with ACE inhibitors were excluded. Patients having a diastolic BP>114 mm Hg, and/or systolic BP>200 mm Hg at screening were excluded. Patients with similar readings at the end of the placebo lead-in period were dropped from further participation in the study. During the placebo lead-in period patients who had signs of bradycardia (<45 bpm) or a resting heart rate of >100 bpm were not advanced to the next stage of the study, but rather dropped from further participation.

Exclusion criteria included the presence or history (past 6 months) of myocardial infarction or cerebrovascular accident and clinically significant cardiac pathology such as congestive heart failure, cardio-genic shock, non-controlled arrhythmias, acute myocarditis or pericarditis, significant valvular or congestive heart disease and unstable angina pectoris; presence or evidence of atrioventricular block (second/third degree), or sick sinus syndrome, or any other conduction defect or abnormality including the presence/history of atrial fibrillation or flutter, associated with pre-excitation syndrome; clinically significant gastrointestinal disease, renal insufficiency (serum creatinine >115 mmol/L), hepatic disease, or electrolyte imbalance (serum potassium <3.5 or >5.3 mmol/L, serum sodium <136->145 mmol/L); presence of bronchial asthma or chronic obstructive pulmonary disease; or the presence of any clinically significant concomitant disease that in the opinion of the investigator could interfere with the patient's participation in the study, or confound the outcome variables. Patients having any clinically significant concomitant disease that could interfere with the patient's participation in the study, or confound the outcome variables were excluded. Patients with a history of alcohol abuse or illicit drug use in the 12 months prior to beginning this protocol were excluded. Patients with a terminal illness were excluded. Patients with an arm circumference >41 cm were excluded. Pregnant females, women who were breast-feeding or women of child-bearing potential must have used adequate contraception. Patients who have had therapy with an investigational compound within 30 days prior to entry into the study were excluded. The use of the following medications was cause for exclusion, each had to have been safely discontinued prior to the placebo lead-in phase of the study, and must been withheld until the protocol had been completed: all diuretics and antihypertensive drugs (including beta-blockers, calcium-channel blockers, vasodilators, ACE inhibitors), MAO inhibitors, all anti-arrhythmic drugs, digitalis, major tranquilizers, antidepressants, cimetidine, corticosteroids, and antineoplastics. Patients gave informed consent. Further exclusion criteria are any of the contraindication listed in the Product Prescribing Information for Vitamin $B_6$ (PDR, 57, 2003:590, 926, 1894, 3221, 3237).

Treatment Schedule—Table 1 shows the study treatment schedule by clinic. Essentially, all patients completed a fixed four-week placebo lead-in, to qualify for initiation of active treatment. Eligible patients then began treatment with 250 mg/day of P5P. This dose was administered orally on a daily basis for the next two (2) weeks, subject to dose-limiting side-effects, after which patients were force-titrated to 500 mg/day of P5P. Again, after two weeks of treatment at the 500 mg/day dose level and subject to dose-limiting side-effects all patients were forced-titrated to 750 mg/day of P5P and maintained at this dose level in the absence of dose-limiting side-effects for the next two weeks. Thereafter and for the final four weeks of the study, all patients were treated with placebo medication. Total study duration for any one patient was 14 weeks with twelve clinic visits. Patients who were on anti-lipid medication prior to the initiation of the study continued their anti-lipid regime throughout the study.

TABLE 1

Study Treatment Schedule by Clinic Visit

| Period | Period Description | | Week | DAY | Visit # |
|---|---|---|---|---|---|
| | SCREENING | | 0 | −21 to −3 | 1 |
| Placebo | Lead-In | Begin | 1 | 0 | 2 |
| | | | 2 | 8-14 | 3 |
| | | | 3 | 15-21 | |
| | | End | 4 | 28 | 4 |
| Active Treatment Period | 250 mg P5P | Begin | 4 | | |
| | | | 4 weeks + 3 days | 31 | 5 |
| | | | 5 | 35 | |
| | | End | 6 | 42 | 6 |
| | 500 mg P5P | Begin | 6 | | |
| | | | 6 weeks + 3 days | 45 | 7 |
| | | | 7 | 49 | |
| | | End | 8 | 56 | 8 |
| | 750 mg P5P | Begin | 8 | | |
| | | | 8 weeks + 3 days | 59 | 9 |
| | | | 9 | 63 | |
| | | End | 10 | 70 | 10 |
| Placebo | Lead-Out | Begin | 10 | | |
| | | | 12 | 84 | 11 |
| | | End | 14 | 98 | 12 |

Primary Efficacy Evaluations
  Supine diastolic blood pressure (SUDBP) measured at specified intervals; and
  Triglyceride, total cholesterol, LDL cholesterol, and HDL levels measured at specified intervals.

Secondary Efficacy Evaluations
  Supine systolic blood pressure (SUSBP) measured at specified intervals; and
  Standing systolic and diastolic blood pressure (STSBP/STDBP), immediate and delayed, measured at specified intervals.

Safety Assessments
  Physical examination, full and brief;
  Laboratory evaluations: CBC, blood chemistries including total bilirubin, creatinine, SGOT, SGPT, alkaline phosphatase, BUN, serum glucose, total protein, electrolytes (including sodium, potassium, and chloride), and blood lipids, folic acid, and serum homocysteine levels, and urinalysis;

12-lead ECG, with interpretation;

Adverse events, recorded at every visit; and

Concomitant medications, recorded at every visit.

Efficacy Evaluations—In general, the following evaluations for drug efficacy are performed.

Supine systolic blood pressure (SUSBP)

Supine diastolic blood pressure (SUDBP)

Standing (IMMEDIATE) systolic blood pressure (STiSBP)

Standing (IMMEDIATE) diastolic blood pressure (STiDBP)

Standing (DELAYED, 2 minutes) systolic blood pressure (STdSBP)

Standing (DELAYED, 2 minutes) diastolic blood pressure (STdDBP)

triglycerides level

Total cholesterol level

LDL cholesterol level

HDL cholesterol level

Dosage Regimens—All patients received treatment medication once daily, in the morning one hour before breakfast. At each dosing, the prescribed number of tablets were taken orally, with water, to allow for the following dosing levels:

| Study Drugs | Dosing Regimen |
|---|---|
| PLACEBO LEAD-IN | |
| 1 Placebo Tablet = | Placebo for 250 mg P5P, OD (morning) |
| ACTIVE | |
| 1 P5P 250 mg Tablet = | 250 mg P5P, OD (morning) |
| 2 P5P 250 mg Tablets = | 500 mg P5P, OD (morning) |
| 3 P5P 250 mg Tablets = | 750 mg P5P, OD (morning) |
| PLACEBO LEAD-OUT | |
| Placebo Tablet = | Placebo for 250 mg P5P, OD (morning) |

The first dose of study medication was administered at clinic under the supervision of clinic personnel. Patients previously on anti-lipid therapy continued their anti-lipid regime unchanged throughout the study.

Duration of Treatment—Each patient was administered placebo or active treatment for a total period of 14 weeks after a successful eligibility assessment.

Results—On average, hypertensive patients taking P5P had reductions in serum triglyceride levels.

As shown in Table 2, hypertensive diabetic patients on P5P therapy had on average, improved triglyceride levels at the end of the 14 week study period. On average, P5P therapy reduced triglyceride levels by approximately 22.1%. As shown in Table 3, the triglyceride lowering effect of effect of P5P therapy was more pronounced in patients having elevated triglyceride levels (>150 mg/dL) prior to the commencement of the study. On average, P5P therapy reduced triglyceride levels by approximately 25.7% in patients having elevated triglyceride levels prior to the commencement of the study.

TABLE 2

P5P Therapy

| | Triglycerides (mg/dL) | |
|---|---|---|
| Patient # | Visit 1 | Visit 12 |
| 16 | 107 | 101 |
| 18 | 530 | 286 |
| 19 | 134 | 97 |
| 20 | 442 | 302 |
| 21 | 197 | 213 |
| 22 | 96 | 142 |
| 28 | 150 | 166 |
| 29 | 601 | 268 |
| 30 | 188 | 160 |
| 31 | 82 | 67 |
| 32 | 180 | 305 |
| Average | 246.1 | 191.5 |
| Percentage Difference | | −22.1% |

TABLE 3

P5P Therapy with Patients having Elevated Triglycerides (>150 mg/dL)

| | Triglycerides (mg/dL) | |
|---|---|---|
| Patient # | Visit 1 | Visit 12 |
| 18 | 530 | 286 |
| 20 | 442 | 302 |
| 21 | 197 | 213 |
| 28 | 150 | 166 |
| 29 | 601 | 268 |
| 30 | 188 | 160 |
| 32 | 180 | 305 |
| Average | 326.9 | 242.9 |
| Percentage Difference | | −25.7% |

The study also investigated the effect of concomitant P5P and statin therapy. As shown in Table 4, all patients on concomitant P5P and statin therapy except for one, showed improved triglyceride levels at the end of the 14 week study. On average, concomitant P5P and statin therapy reduced triglyceride levels by approximately 25.2%.

TABLE 4

Concomitant P5P and Statin Therapy

| | Triglycerides (mg/dL) | |
|---|---|---|
| Patient # | Visit 1 | Visit 12 |
| 17 (Lipitor) | 255 | 179 |
| 23 (Lipitor) | 164 | 212 |
| 24 (Pravachol) | 667 | 365 |
| 25 (Zocor) | 222 | 187 |
| 27 (Zocor) | 96 | 107 |
| Average (all statins) | 280.8 | 210.0 |
| Percentage Difference | | −25.2% |

Example Two

P5P Treatment Lowers Triglyceride Levels in Hypercholesteremic Rabbits

The anti-atherogenic effects of P5P alone and in combination with simvastatin in a rabbit hypercholesteremic model were determined. The study compared the effects of P5P and simvastatin alone and in combination on atherosclerotic lesion formation, lipid profile (total cholesterol, LDL, HDL, triglycerides and oxidized LDL), homocysteine levels and various markers of inflammation (CRP, IL-1β, IL-6, IFN-γ and TNF-α).

Animals—Male New Zealand white rabbits 2.0-3.0 kg.

Animal Feed—The normocholesterol diet is Co-op Complete Rabbit Feed manufactured by Federated Co-operatives Limited (Saskatchewan). The 2% cholesterol diet is Test Diet 0009459 MRab/2% Chol 3/16 manufactured by Purina Mills (USA).

The rabbits were fed the normocholesterol and 2% cholesterol diet ad libitum. All animals received a timothy cube after blood sampling.

Study Design—Prior to the start of the study, rabbits are randomly assigned to one of the following groups (n=9 per group):

Group 1: Normocholesterol diet (normal)

Group 2: Hypercholesterol diet (control)

Group 3: Hypercholesterol diet+P5P 10 mg/kg/day

Group 4: Hypercholesterol diet+simvastatin 5 mg/kg/day

Group 5: Hypercholesterol diet+P5P 10 mg/kg/day+simvastatin 5 mg/kg/day

The rabbits were fed a normocholesterol or hypercholesterol diet for a total of 7 weeks. The normocholesterol rabbits were treated once per day with 1 ml of ethanol and 5 ml of RO water via a nasogastric tube. The hypercholesterol animals were treated once per day with either P5P (10 mg/kg), simvastatin (5 mg/kg) or a combination of P5P and simvastatin (P5P 10 mg/kg; simvastatin 5 mg/kg) via a nasogastric tube. The P5P was dissolved in 5 ml of 0.05 N NaOH so that the pH of the solution is approximately 7. The simvastatin was dissolved in 1 ml of anhydrous ethanol.

TABLE 5

Test Compound Diluents

| Group | Diluent (small vial) | Diluent (large vial) |
| --- | --- | --- |
| Normo | 1 ml ethanol | 5 ml RO water |
| Hyper | 1 ml ethanol | 5 ml RO water |
| Hyper + P5P | 1 ml ethanol | 5 ml 0.05 N NaOH |
| Hyper + Sim | 1 ml ethanol | 5 ml RO water |
| Hyper + Sim + P5P | 1 ml ethanol | 5 ml 0.05 N NaOH |

Five ml of blood was collected from the marginal ear vein of the rabbits at 0, 2, 4 and 6 weeks. Prior to blood collection the animals were sedated with 1 mg/kg of acepromazine. Following collection, the serum was separated. The serum is aliquoted (500 µl) and frozen at −80° C. until used for the assaying various lipids (total cholesterol, LDL, HDL, triglycerides, oxidized LDL) and cytokines (CRP, IL-1β, IL-6, IFN-γ and TNF-α).

At 7 weeks, the animals were anesthetized and 10 ml of blood was collected. Then the animals were euthanized, and the heart and thoracic aorta removed. The hearts and aortas were frozen in liquid nitrogen or an ethanol dry ice bath and frozen in liquid nitrogen or an ethanol dry ice bath and stored at −80° C. until analyzed.

Test Articles—P5P (pyridoxal 5'-phosphate monohydrate) was purchased from Sigma (P82870). Simvastatin is obtained from ACIC Fine Chemicals Inc. Two test compound vials were provided for each animal for each day. The first vial (small) was diluted in 1 ml of anhydrous ethanol. The second vial was diluted in either 5 ml of RO water or 5 ml of 0.05 N NaOH. The diluent for each vial was clearly marked on the vial. The test solutions were prepared fresh each day just before they were administered to the animals. The stock P5P was stored in a refrigerator at 4° C. under low light conditions. The simvastatin was stored following the manufacture recommendations. The individual test vials were stored in a refrigerator at 4° C. under low light conditions.

Test Article(s) Dose, Route of Administration and Duration—The rabbits were treated orally with the drugs, once per day for a total of 7 weeks. The contents of vial one (small; 1 ml) were given to the animals first, followed by the contents of vial 2 (large; 5 ml). The test compound treatments were followed by a 5 ml RO water chaser.

Results—At the end of the 7 week study period, rabbits fed the hypercholesterol diet (control) showed significant elevations in serum triglyceride levels as compared to rabbits fed the normal diet (normal). The serum triglyceride levels for the control rabbits was more than 3 times greater than the serum triglyceride levels observed in the normal rabbits (see FIG. 1).

Figure 1:
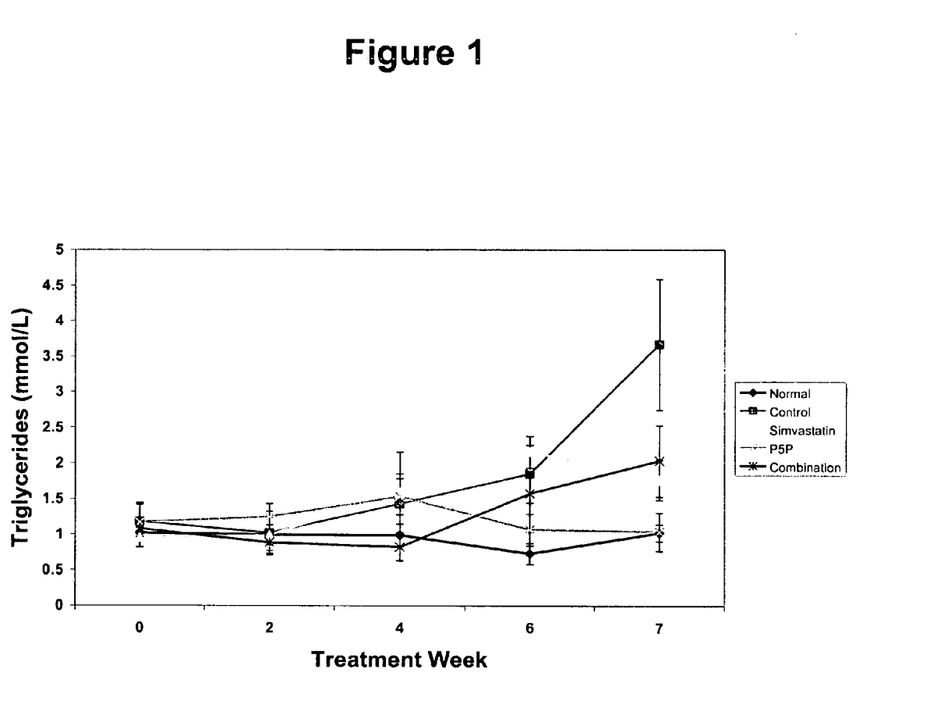
FIG. 1 is a line graph comparing serum triglyceride levels in normal rabbits (♦) (rabbits fed a normocholesterol diet and not treated), control rabbits (■) (rabbits fed a hypercholestrol diet and not treated), and rabbits fed a hypercholesterol diet and treated with simvastatin therapy (star), pyridoxal-5'-phosphate (P5P) therapy (X), and simvastatin+P5P combination therapy (*) over a seven week period.

Simvastatin therapy, P5P therapy and simvastatin+P5P combination therapy were all effective in reducing serum triglyceride levels in rabbits fed the hypercholesterol diet. Serum triglyceride levels in rabbits treated with simvastatin, P5P, and simvastatin+P5P were lower than the serum triglyceride levels for the untreated control rabbits.

Figure 2:
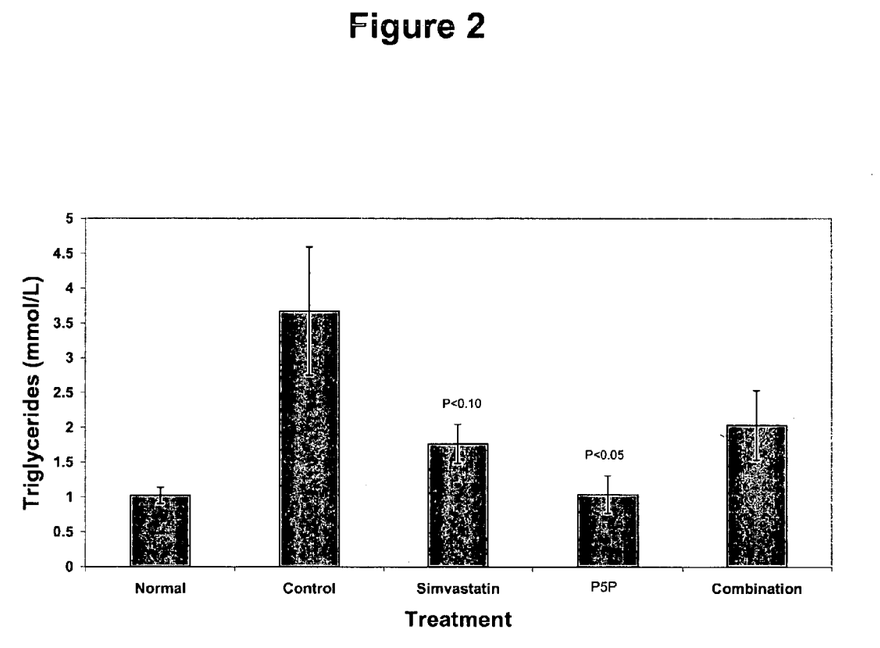
FIG. 2 is a bar graph comparing average serum triglyceride levels in rabbits following seven weeks of simvastatin therapy, P5P therapy, or simvastatin+P5P combination therapy.

As shown in FIG. 2 and Table 6, P5P treatment was found to be more effective than simvastatin treatment in reducing serum triglyceride levels. The average serum triglyceride levels observed for the P5P treated rabbits were similar to the average serum triglyceride levels observed for the rabbits fed the normal diet. At the end of the 7 week study period, the average serum triglyceride levels for the P5P treated rabbits were about ⅓ of the levels observed in the control rabbits. In comparison, the average serum triglyceride levels for the simvastatin treated rabbits were about ½ of the levels observed in the control rabbits. Combining simvastatin with P5P produced similar reductions in serum triglyceride levels as observed with P5P alone.

TABLE 6

Simvastatin therapy, P5P therapy, and simvastatin + P5P combination therapy

Triglycerides (mmol/L)

| Week | Normal (n = 8) | Control (n = 7) | Simvastatin (n = 5) | P5P (n = 5) | Combination (n = 5) |
| --- | --- | --- | --- | --- | --- |
| 0 | 1.020 | 1.180 | 0.956 | 1.168 | 1.078 |
| 2 | 0.994 | 1.019 | 0.986 | 1.244 | 0.885 |
| 4 | 0.989 | 1.429 | 1.588 | 1.530 | 0.823 |
| 6 | 0.731 | 1.850 | 2.158 | 1.066 | 1.577 |
| 7 | 1.023 | 3.671 | 1.766 | 1.038 | 2.033 |

Example Three

Phase II Clinical Study: Effectiveness of P5P and Lisinopril Therapy in Hypertensive Diabetic Patients Objective—A phase II clinical study was conducted to determine the effects of pyridoxal-5'-phosphate in combination with lisinopril on blood pressure and metabolic function in hypertensive patients with type 2 diabetes.

Summary of Study Design—The phase II study was a randomized, parallel group, cross-over, double-blinded to study medication, placebo-controlled comparison of P5P BID at total daily doses of 100, 300, or 1000 mg alone and in combination with 20 mg lisinopril given once daily (QD). In order to protect against antihypertensive and metabolic carry-over effects of lisinopril, all patients were randomized in 2 different treatment sequences. Patients randomized in the first treatment sequence receive an 8-week treatment with lisinopril 20 mg and P5P (or placebo) and then an 8-week treatment with P5P alone (or placebo). Patients randomized in the second treatment sequence receive an 8-week treatment with P5P alone and then an 8-week treatment with lisinopril 20 mg and P5P (or placebo). In each treatment sequence, all patients were randomized to P5P at the different prespecified dosages.

Mean trough sitting and standing BP were measured at each visit. Twenty-four hour ambulatory BP monitoring (ABPM) were performed at Visit 2 prior to randomization (end of washout period) and after week 8 (Visit 5) and week 16 (Visit 8) weeks of active therapy. Laboratory tests were performed at screening (Visit 1), prior to randomization (Visit 2), at week 2 (Visit 3a), week 8 (Visit 5), week 10 (Visit 6a), and at week 16 (Visit 8).

A physical examination and an electrocardiogram were performed at screening (Visit 1) and at the end of the study (Visit 8).

Patients with a mean trough SiSBP >180 mmHg at anytime following randomization have repeated measurements within 24 hours. If the mean trough SiSBP is >180 mmHg at the following visit, the patient was discontinued from the study and appropriate therapy was instituted.

Patients with a mean trough SiDBP >110 mmHg at anytime during the study have repeated measurements performed within 24 hours. If the mean trough SiDBP remains >110 mmHg, then the patient was discontinued from the study and appropriate therapy was instituted.

Patients with a mean trough SiSBP of >160 mm Hg four (4) weeks after randomization have repeated measurements within 48 hours. If the mean trough SiSBP was >160 mmHg at the following visit, the patient was discontinued from the study and appropriate therapy was instituted. These patients were part of the safety evaluation.

Patients with a mean trough SiDBP of 105 mm Hg four (4) weeks after randomization have repeated measurements within 48 hours. If the mean trough SiDBP was >105 mmHg at the following visit, the patient was discontinued from the study and appropriate therapy was instituted. These patients were part of the safety evaluation.

Treatment Plan—Two to Four-week Washout (Baseline) Period: Patients were instructed on the proper procedure for discontinuing their current antihypertensive medications (discontinuation or tapering) according to the manufacturer's label specifications. If a patient's current antihypertensive treatment needed to be tapered earlier, the Investigator complied with the corresponding timelines before randomization. With the exception of any tapering off of prior therapy, if any, no other anti-hypertensive medication was given to the patient during the washout period. Patients continued any existing diabetic treatment with sulfonylureas (tolbutamide, tolazamide, acetohexamide, chlorpropamide and second generation glyburide, glipizide, glimepiride), D-Phenylalanine derivatives, metformin, thiazolidinediones, acarbose, miglitol, and/or insulin throughout the study. Patients received placebo to be taken twice daily during the washout period. Standard diabetic medication was maintained throughout study. The duration of the washout period was two to four weeks, at the discretion of the Investigator taking into consideration whether the patient's blood pressure had stabilized following removal of any prior antihypertensive medication.

Active (Study) Medication Period: After the washout period, eligible patients were randomized to one of the 2 following sequences of treatment for 16 weeks.

Week 0 to 8: Treatment period (P5P alone (or placebo) or P5P (or placebo) and Lisinopril)

Week 8 to 16: Treatment period (P5P alone (or placebo) or P5P (or placebo) and Lisinopril)

Study Groups—The patients were randomized into one of four groups:

Group A)

Sequence 1 Placebo and then Placebo+Lisinopril 20 mg

Sequence 2 Placebo+Lisinopril 20 mg and then Placebo alone

Group B)

Sequence 1 P5P 100 mg and then P5P 100 mg+Lisinopril 20 mg

Sequence 2 P5P 100 mg+Lisinopril 20 mg and then P5P 100 mg alone

Group C)

Sequence 1 P5P 300 mg and then P5P 300 mg+Lisinopril 20 mg

Sequence 2 P5P 300 mg+Lisinopril 20 mg and then P5P 300 mg alone

Group D)

Sequence 1 P5P 1000 mg and then P5P 1000 mg+Lisinopril 20 mg

Sequence 2 P5P 1000 mg+Lisinopril 20 mg and P5P 1000 mg alone

All medications were taken at the same time each day during washout and treatment periods:

P5P/placebo: morning dose: 7:00 am to 11:00 am evening dose: 7:00 pm to 11:00 pm Lisinopril: 7:00 am to 11:00 am (with P5P/placebo morning dose)

On the day of a clinic visit, all study medication for that morning was taken following the completion of all study parameters scheduled.

Efficacy Measurements—Blood pressure was measured using a sphygmomanometer maintained in good condition (standard mercury, Bp-Thru, Omron) to measure blood pressure. Care was taken to standardize measurements by adhering to a rigorous and detailed protocol.

Other Efficacy Endpoints—Analytical efficacy measurements, including markers of metabolic function (insulinemia, fasting serum glucose, glycated hemoglobin, LDL, HDL, non-HDL and triglycerides), endothelial function (ICAM-1, VCAM-1, E-selectin and albuminuria), kidney function (creatinine, glomular filtration rate), CRP and homocysteine, were conducted on blood samples taken on Visits 2, 5 and 8. Samples were sent to a central laboratory for analysis.

Results—As shown in Table 7, on average diabetic hypertensive patients taking 300 mg and 1000 mg doses of P5P had reductions in serum triglyceride (TG), low density lipids (LDL), non-HDL and total cholesterol (TC) levels.

Figure 3:
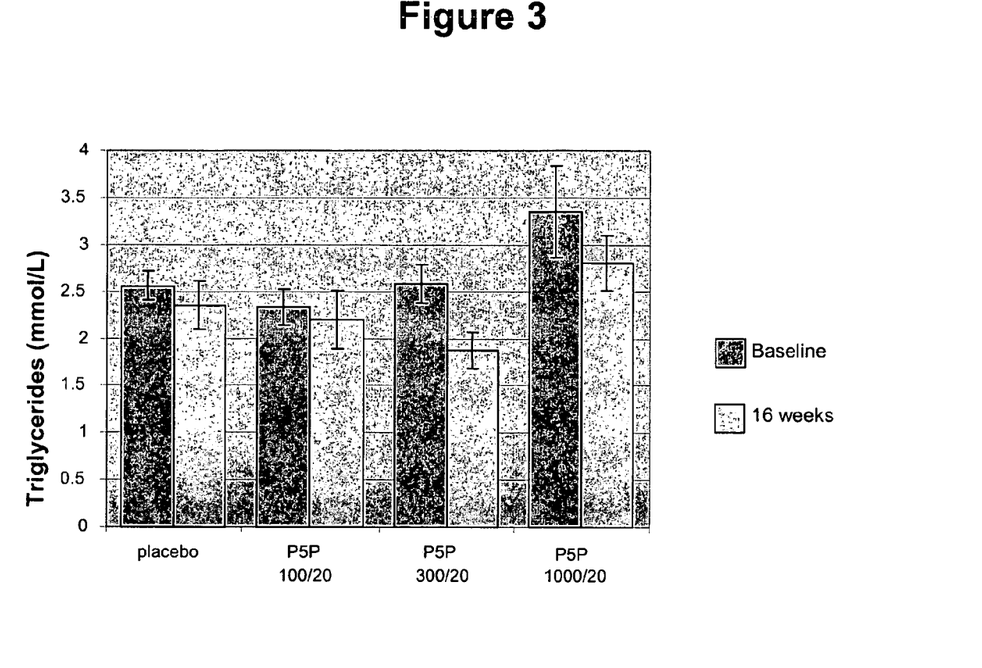
FIG. 3 is a bar graph comparing average serum triglyceride levels in diabetic hypertensive patients following 16 weeks of combination therapy of P5P and lisinopril.
Figure 4:
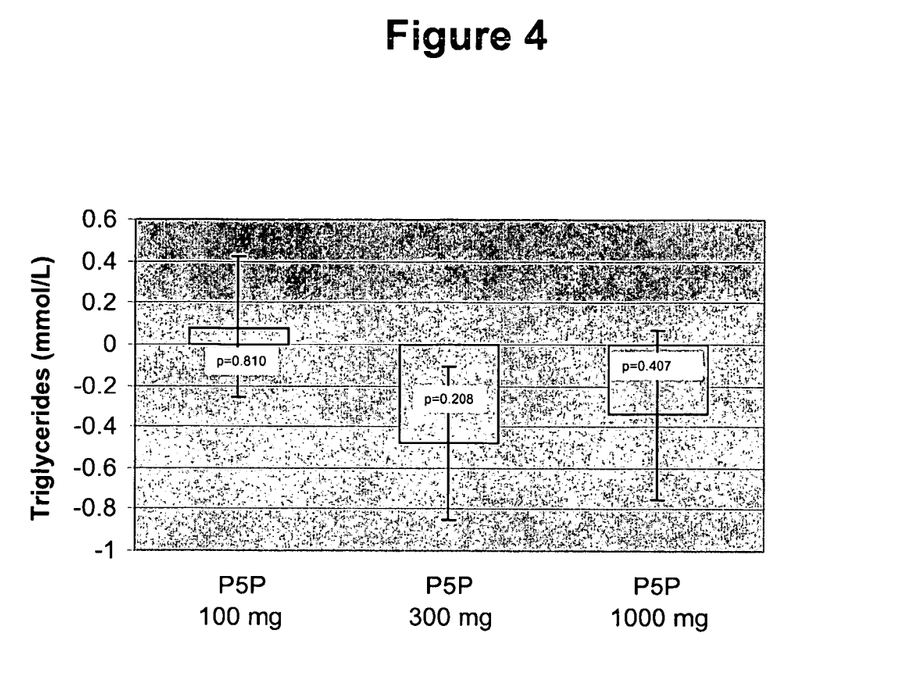
FIG. 4 is a bar graph comparing average reductions in serum serum triglyceride levels in diabetic hypertensive patients following 16 weeks of combination therapy of P5P and lisinopril.

As shown in FIGS. 3 and 4 and table 7, hypertensive diabetic patients with elevated triglyceride (TG) levels (>1.7 mmol/L) at baseline showed a reduction in serum TG levels of about 0.70 mmol/L vs. baseline for patients taking 300 mg of P5P and about 0.56 mmol/L vs. baseline for patients taking 1000 mg of P5P.

As shown in Table 7, P5P therapy also resulted in decreases in serum LDL levels, with an average reduction of 0.27 mmol/L (placebo corrected) for patients taking 300 mg or 1000 mg of P5P. In patients having elevated LDL levels (>2.59 mmol/L), on average, patients taking 300 mg of P5P showed a reduction in serum LDL levels of about 0.41 mmol/L and patients taking 1000 mg of P5P showed reduction in serum LDL levels of about 0.53 mmol/L.

As shown in Table 7, P5P therapy also resulted in decreases in total serum cholesterol (TC) levels. In patients having elevated TC levels (>5.15 mmol/L), on average, patients taking 300 mg of P5P showed a reduction in serum TC levels of about 0.91 mmol/L (placebo corrected) reduction and patients taking 1000 mg of P5P showed reduction in serum TC levels of about 1.03 mmol/L (placebo corrected).

As shown in table 7, the therapy also resulted in a decrease in Non-HDL. In patients with non-HDL >3.34 mmol/L at baseline, there was a reduction in non-HDL of 0.68 mmol/L compared to baseline for patients on 300 mg. For patients taking 1000 mg with non-HDL. 3.34 mmol/L there was a decrease of 0.71 mmol/L vs. baseline.

wherein
$R_1$ is alkyl,
  alkenyl,
    in which alkyl or alkenyl can be interrupted by nitrogen, oxygen, or sulfur, and can be unsubstituted or substituted at the terminal carbon by hydroxy, alkoxy, alkanoyloxy, alkanoyloxyaryl, alkoxyalkanoyl, alkoxycarbonyl, or dialkylcarbamoyloxy;
alkoxy;
dialkylamino;
alkanoyloxy;
alkanoyloxyaryl;

TABLE 7

Effect of Lisinopril/P5P Therapy On Lipid Profile

| Lipids | Plasma levels | P5P 300 mg | P5P 1000 mg |
|---|---|---|---|
| Normal TG | <1.7 mmol/L | −0.70 mmol/L (p = 0.04)b | −0.56 mmol/L (p = 0.12)b |
| Borderline-high TG | 1.7-2.3 mmol/L | −0.48 mmol/L (p = 0.208)p | −0.34 mmol/L (p = 0.407)p |
| High TG | 2.3-5.7 mmol/L | (16 wk vs. baseline for TG | (16 wk vs. baseline for TG |
| Very high TG | ≧5.7 mmol/L | ≧1.7 mmol/L) | ≧1.7 mmol/L) |
| Optimal LDL | <2.6 mmol/L | −0.15 mmol/L (p = 0.194)b | −0.15 mmol/L (p = 0.197)b |
| Normal (near opti.) LDL | 2.6-3.3 mmol/L | −0.27 mmol/L (p = 0.095)p | −0.27 mmol/L (p = 0.095)p |
| Borderline-high LDL | 3.4-4.1 mmol/L | (LDL non-stratified | (LDL non-stratified data: |
| High LDL | 4.1-4.9 mmol/L | data: 16 wk vs. baseline) | 16 wk vs. baseline) |
| Very high LDL | ≧4.9 mmol/L | | |
| LDL >2.59 mmol/L | | −0.41 mmol/L (p = 0.04) (12% reduction) | −0.53 mmol/L (p = 0.075) |
| Desirable TC | <5.2 mmol/L | −0.18 mmol/L (p = 0.273)b | −0.29 mmol/L (p = 0.075)b |
| Borderline-high TC | 5.2-6.2 mmol/L | −0.28 mmol/L (p = 0.188)p | −0.39 mmol/L (p = 0.065)p |
| High TC | ≧6.2 mmol/L | (TC non-stratified) | (TC non-stratified) |
| TC >5.18 mmol/L | | −0.91 mmol/L (p = 0.02) (15.7%)b | −1.03 mmol/L (p = 0.001)b |
| Non-HDL | Calculated number. Not measured in plasma | −0.21 mmol/L (p=)b −0.27 mmol/L (p=)p (HDL non-stratified) | −0.26 mmol/L (p = 0.089)b −0.32 mmol/L (p = 0.119)p (HDL non-stratified) |
| Non HDL >3.34 mmol/L | | −0.68 mmol/L (p = 0.029) (15%)b | −0.71 mmol/L (p = 0.007)b |

To convert mmol/L to mg/dL multiply by 38.7 for cholesterol and 88 for triglycerides.
b—baseline;
p - placebo corrected

What is claimed is:

1. A method of treating hypertriglyceridemia comprising administering a therapeutically effective amount for treating hypertriglyceridemia of a compound selected from the group consisting of pyridoxal, pyridoxal-5'-phosphate, pyridoxamine, a 3-acylated analogue of pyridoxal, a 3-acylated analogue of pyridoxal-4,5-aminal, a pharmaceutically acceptable salt thereof, and a mixture thereof to a patient in need thereof;
  a) wherein the 3-acylated analogue of pyridoxal comprises:

alkoxyalkanoyl;
alkoxycarbonyl;
dialkylcarbamoyloxy;
aryl,
  in which aryl can be substituted by alkyl, alkoxy, amino, hydroxy, halo, nitro, or alkanoyloxy;
aryloxy;
arylthio; or
aralkyl; and
  b) wherein the 3-acylated analogue of pyridoxal-4,5-aminal comprises:

wherein
R₁ is alkyl,
  alkenyl,
    in which alkyl or alkenyl can be interrupted by nitrogen, oxygen, or sulfur, and can be unsubstituted or substituted at the terminal carbon by hydroxy, alkoxy, alkanoyloxy, alkanoyloxyaryl, alkoxyalkanoyl, alkoxycarbonyl, or dialkylcarbamoyloxy;
  alkoxy;
  dialkylamino;
  alkanoyloxy;
  alkanoyloxyaryl;
  alkoxyalkanoyl;
  alkoxycarbonyl;
  dialkylcarbamoyloxy;
  aryl,
    in which aryl can be substituted by alkyl, alkoxy, amino, hydroxy, halo, nitro, or alkanoyloxy;
  aryloxy;
  arylthio; or
  aralkyl; and
R₂ is of the formula wherein $R_3$ and $R_4$ are each independently alkyl, alkenyl, cycloalkyl, aryl, or, when $R_3$ and $R_4$ are taken together to form a ring with the nitrogen atom, which may optionally be interrupted by a heteroatom,
or a pharmaceutically acceptable acid addition salt thereof.

2. The method according to claim 1, wherein the compound is pyridoxal-5-phosphate.

3. The method according to claim 1, wherein the hypertriglyceridemia is primary hypertriglyceridemia.

4. The method according to claim 1, wherein the patient has diabetes.

5. The method according to claim 1, wherein the hypertriglyceridemia is secondary hypertriglyceridemia.

6. The method according to claim 5, wherein the secondary hypertriglyceridemia is drug related.

7. The method according to claim 6, wherein the drug is selected from the group consisting of alcohol, a diuretic, a β-blocker, an angiotensin converting enzyme inhibitor, an estrogen replacement therapy, an oral contraceptive, an estrogen receptor modulator, a retinoid, an immunosuppressant, an antiretroviral, a protease inhibitor, an antipsychotic, and a combination thereof.

8. The method according to claim 2, wherein the therapeutically effective amount of pyridoxal-5'-phosphate is between 0.5 and 50 mg/kg body weight.

9. The method according to claim 2, wherein the therapeutically effective amount of pyridoxal-5'-phosphate is between 1 and 15 mg/kg body weight.

10. The method according to claim 1, wherein the patient is human.

11. The method according to claim 1, further comprising administering a therapeutically effective amount of a lipid lowering agent selected from the group consisting of a nicotinic acid, a fibrate, a HMG CoA reductase inhibitor, a cholesteryl ester transfer protein inhibitor, and a combination thereof.

12. The method according to claim 11, wherein the nicotinic acid is niacin.

13. The method according to claim 11, wherein the fibrate is selected from the group consisting of bezafibrate, clofibrate, ciprofibrate, fenofibrate, and gemifibrozil, and a mixture thereof.

14. The method according to claim 11, wherein the HMG CoA reductase inhibitor is selected from the group consisting of pravastatin, lovastatin, fluvastatin, atorvastatin, simvastatin, rosuvastatin, velostatin, fluindostatin and a mixture thereof.

15. The method according to claim 11, wherein the cholesteryl ester transfer protein inhibitor is torcetrapib or JTT-705, which has the structure 16. The method according to claim 1, further comprising administering a therapeutically effective amount of an ACE inhibitor selected from the group consisting of benazepril; captopril; cilazapril; enalapril; enalaprilat; fosinopril; lisinopril; moexipril; perindopril; quinapril; ramipril; trandolapril; and a mixture thereof.

17. The method according to claim 16, wherein the ACE inhibitor is lisinopril.

18. The method according to claim 17, wherein the therapeutically effective amount of lisinopril is between 5 and 40 mg per day.

19. The method according to claim 17, wherein the therapeutically effective amount of lisinopril is 20 mg per day.

* * * * *